(12) United States Patent
Shriyan et al.

(10) Patent No.: US 10,018,579 B1
(45) Date of Patent: Jul. 10, 2018

(54) SYSTEM AND METHOD FOR CATHODOLUMINESCENCE-BASED SEMICONDUCTOR WAFER DEFECT INSPECTION

(71) Applicant: KLA-Tencor Corporation, Milpitas, CA (US)

(72) Inventors: Sameet K. Shriyan, San Jose, CA (US); Hong Xiao, Pleasanton, CA (US); David Kaz, Oakland, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/255,024

(22) Filed: Sep. 1, 2016

Related U.S. Application Data

(63) Continuation-in-part of application No. 15/047,495, filed on Feb. 18, 2016, now abandoned.

(60) Provisional application No. 62/117,849, filed on Feb. 18, 2015.

(51) Int. Cl.
*G01N 23/2254* (2018.01)

(52) U.S. Cl.
CPC .  *G01N 23/2254* (2013.01); *G01N 2223/6116* (2013.01); *G01N 2223/646* (2013.01)

(58) Field of Classification Search
CPC ....... G01N 23/2254; G01N 2223/6116; G01N 2223/646; H01J 37/26
See application file for complete search history.

(56) References Cited

U.S. PATENT DOCUMENTS

| 4,238,686 A | 12/1980 | Chin et al. |
| 4,900,932 A | 2/1990 | Schafer et al. |
| 4,929,041 A * | 5/1990 | Vahala ................. H01J 37/228 250/227.23 |

(Continued)

FOREIGN PATENT DOCUMENTS

| JP | 2007071646 A | 3/2007 |
| JP | 2011133446 A | 7/2011 |
| WO | 2013151421 A2 | 10/2013 |

OTHER PUBLICATIONS

Mendez, Bianchi, et al., "Influence of Te concentration on the infrared cathodoluminescence of GaAs:Te wafers", Journal of Applied Physics, Mar. 1, 1991, pp. 2776-2779, vol. 69-No. 5, American Institute of Physics, Madrid, Spain.

(Continued)

*Primary Examiner* — Eliza Osenbaugh-Stewar
(74) *Attorney, Agent, or Firm* — Suiter Swantz pc llo

(57) ABSTRACT

A system for measuring cathodoluminescence from a substrate includes an electron beam source configured to generate an electron beam, a sample stage configured to secure a sample and an electron-optical column including a set of electron-optical elements to direct at least a portion of the electron beam through onto a portion of the sample. The system also includes a set of guide optics located at a position within or below the electron-optical column and a set of collection optics, wherein the set of guide optics captures cathodoluminescent light emitted from the sample in response to the electron beam and directs the cathodoluminescent light to the set of collection optics. In addition, the system includes a detector. The set of collection optics is configured to image the cathodoluminescent light onto the detector.

24 Claims, 4 Drawing Sheets

(56) References Cited

U.S. PATENT DOCUMENTS

| | | | |
|---|---|---|---|
| 5,047,370 A | 9/1991 | Yamamoto et al. | |
| 5,264,704 A | 11/1993 | Phang et al. | |
| 7,589,322 B2 | 9/2009 | Nishikata et al. | |
| 8,853,672 B2 | 10/2014 | Yamamoto | |
| 8,895,921 B2 | 11/2014 | Kruit et al. | |
| 8,895,922 B2 | 11/2014 | Berney | |
| 8,912,509 B2 | 12/2014 | Mathieu Kociak et al. | |
| 8,933,402 B2 | 1/2015 | Shimizu | |
| 8,963,165 B2 | 2/2015 | Araki et al. | |
| 2007/0023655 A1* | 2/2007 | Nishikata | H01J 37/228 |
| | | | 250/310 |
| 2010/0297790 A1 | 11/2010 | Nakahata et al. | |
| 2011/0117726 A1 | 5/2011 | Pinnington et al. | |
| 2013/0016345 A1 | 1/2013 | Yoshikawa et al. | |
| 2013/0068966 A1* | 3/2013 | Kociak | G01N 23/2254 |
| | | | 250/458.1 |
| 2014/0131573 A1* | 5/2014 | Parker | G01N 21/6428 |
| | | | 250/307 |
| 2014/0339438 A1* | 11/2014 | Correns | G01N 21/64 |
| | | | 250/459.1 |

OTHER PUBLICATIONS

Schubert, Martin C., et al., "Spatially Resolved Luminescence Spectroscopy on Multicrystalline Silicon", 23rd European Photovoltaic Solar Energy Conference and Exhibition, Sep. 1-5, 2008, pp. 17-23, Valencia, Spain.

* cited by examiner

SYSTEM AND METHOD FOR CATHODOLUMINESCENCE-BASED SEMICONDUCTOR WAFER DEFECT INSPECTION

CROSS-REFERENCE TO RELATED APPLICATION

The present patent application constitutes a continuation-in-part application of U.S. Non-Provisional patent application Ser. No. 15/047,495, entitled SYSTEM AND METHOD FOR CATHODOLUMINESCENCE-BASED SEMICONDUCTOR WAFER DEFECT INSPECTION, naming Sameet K. Shriyan, Hong Xiao and David Kaz as inventors, which constitutes a non-provisional (regular) patent application of U.S. Provisional Patent Application Ser. No. 62/117,849, entitled CATHODOLUMINESCENCE FOR SEMICONDUCTOR WAFER DEFECT INSPECTION, naming Sameet K. Shriyan, Hong Xiao, and David Kaz as inventors. Both of the above applications are incorporated herein by reference in their entirety.

TECHNICAL FIELD

The present disclosure generally relates to defect inspection of films, and, more particularly, to cathodoluminescence-based defect inspection of epitaxial grown films.

BACKGROUND

As demand for ever-shrinking semiconductor devices continues to increase, so too will the demand for improved inspection tools. One such inspection technology includes the inspection of films grown on a substrate. Currently, many approaches employed to inspect the quality of substrate grown films are destructive and time consuming. As such, it would be advantageous to provide a system and method that provides time effective and non-destructive inspection of substrate films so as to remedy the shortcomings of the conventional approaches.

SUMMARY

A system for cathodoluminescence-based semiconductor wafer defect inspection is disclosed, in accordance with one or more embodiments of the present disclosure. In one illustrative embodiment, the system includes an electron beam source configured to generate an electron beam. In another illustrative embodiment, the system includes a sample stage configured to secure a sample. In another illustrative embodiment, the system includes an electron-optical column including a set of electron-optical elements to direct at least a portion of the electron beam onto a portion of the sample. In another illustrative embodiment, the system includes a set of guide optics located at a position within or below the electron-optical column. In another illustrative embodiment, the system includes a set of collection optics. In another illustrative embodiment, the system includes a detector. In another illustrative embodiment, the set of guide optics is configured to collect cathodoluminescent light emitted from the sample in response to the electron beam and direct the cathodoluminescent light to the set of collection optics. In another illustrative embodiment, the set of collection optics is configured to image the cathodoluminescent light onto the detector.

A method for cathodoluminescent-based inspection defects disclosed, in accordance with one or more embodiments of the present disclosure. In one illustrative embodiment, the method includes illuminating a substrate with an electron beam. In another illustrative embodiment, the method includes cathodoluminescent light emitted from the substrate in response to the electron beam. In another illustrative embodiment, the method includes imaging the cathodoluminescent light onto a detector. In another illustrative embodiment, the method includes determining one or more characteristics of the substrate based on the imaged cathodoluminescent light.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Figure 1:
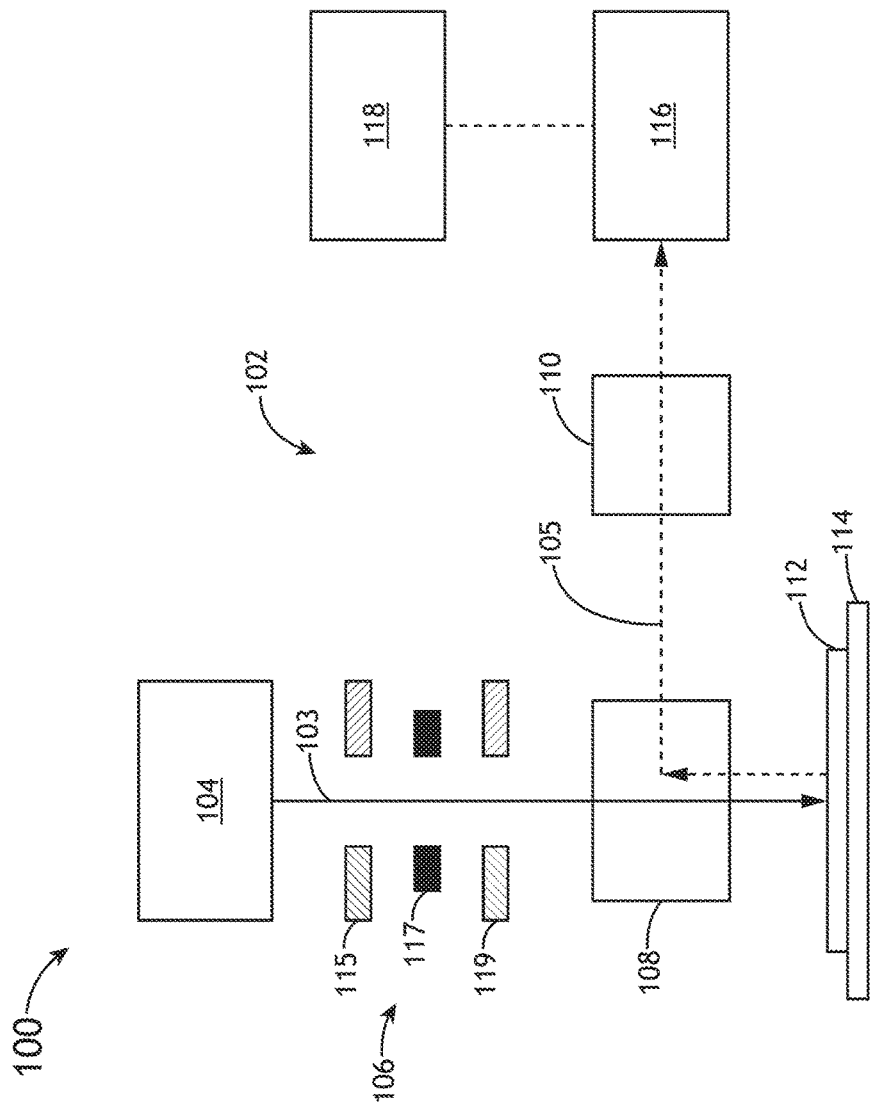
FIG. 1 is a block diagram illustrating a system for measuring cathodoluminescence from a substrate, in accordance with one embodiment of the present disclosure.

Reference will now be made in detail to the subject matter disclosed, which is illustrated in the accompanying drawings.

Referring generally to FIGS. 1 through 4, a system and method for measuring cathodoluminescence for substrate defect inspection is described in accordance with the present disclosure.

Embodiments of the present disclosure are directed to the non-destructive inspection of substrates using cathodoluminescence. For example, embodiments of the present disclose may non-destructively inspect the quality of high carrier mobility materials using cathodoluminescence. For instance, such materials may be epitaxially grown on a substrate, such as a silicon wafer, for advanced technology nodes. Additional embodiments of the present disclosure may be used to inspect patterned or unpatterned (e.g., blanket epitaxial growth) wafers in order to identify sub-surface defects (e.g., defects buried below surface of substrate).

It is noted herein that illuminating an epitaxially grown high mobility carrier material causes cathodoluminescence. Cathodoluminescence occurs because the impingement of a high energy electron beam onto a semiconductor results in the promotion of electrons from the valence band into the conduction band, leaving behind a hole. When an electron and a hole recombine, it is possible for a photon to be emitted. The energy of the photon and the probability that a photon will be emitted depend on the material, the purity of the material, and/or defect state of the material.

Additional embodiments of the present disclosure are directed to an optical system for capturing the cathodoluminescent light emitted from a substrate in response to an incident electron beam. This captured cathodoluminescent light may then be imaged onto a detector in order to reveal defect locations on the substrate. Some embodiments of the present disclosure may capture monochromatic images of the substrate with the cathodoluminescent light, while other embodiments capture panchromatic images of the substrate with the cathodoluminescent light. It is further noted that, in a panchromatic image, defective sites will appear as dark spots and counting the dark spots may reveal the density of defects which will impact device performance. One embodiment of the present disclosure includes an optimized light path for maximum signal collection and routing.

Additional embodiments of the present disclosure provide for spectral decomposition of the measured signal. In this regard, hyperspectral imaging can provide improved spectral resolution (~10 nm). Additional embodiments of the present disclosure are directed to analyzing defect density and/or the number of defects through the analysis of the cathodoluminescence-based imagery data. Additional embodiments of the present disclosure are directed to measuring the temporal decay of the captured cathodoluminescent light signal. Additional embodiments of the present disclosure are directed to performing depth resolved cathodoluminescent light based spectroscopy through the variation of the energy of the electron beam.

It is noted herein that the utilization of cathodoluminescence may reduce the amount of time necessary to inspect films, such as, but not limited to, epitaxial grown films.

FIG. 1 illustrates a block diagram view of system 100 for measuring cathodoluminescence for substrate defect inspection, in accordance with one or more embodiments of the present disclosure.

In one embodiment, the system 100 includes an inspection sub-system 102. In one embodiment, the inspection sub-system 102 includes an electron source 104. For example, the electron source 104 includes one or more electron guns (e.g., a single electron gun or multiple electron guns) for generating one or more electron beams 103. The one or more electron beams 103 impinge on the surface of the sample 112. In response, a cathodoluminescent light signal is generated, which may be collected and analyzed to carry out defect inspection of the substrate 112.

In another embodiment, the inspection sub-system 102 includes an electron-optical column 106. The electron-optical column 106 may include a set of electron-optical elements. The set of electron-optical elements may direct at least a portion of the electron beam 103 to the surface of the substrate 112, such as, but not limited to, a semiconductor wafer (e.g., semiconductor wafer with epitaxial grown film). The set of electron-optical elements of the electron-optical column 106 may include any electron-optical elements known in the art suitable for focusing and/or directing the electron beam 103 to the substrate 112. In one embodiment, the set of electron-optical elements includes one or more electron-optical lenses. For example, the electron-optical lenses may include, but are not limited to, one or more condenser lenses 115 for collecting electrons from the electron beam source 104. By way of another example, the electron-optical lenses may include, but are not limited to, one or more objective lenses 119 for focusing the electron beam 103 onto a selected region of the substrate 112.

For purposes of simplicity, a single electron-optical column 106 is depicted in FIG. 1. It is noted herein that this configuration should not be interpreted as a limitation on the present disclosure. For example, the system 100 may include multiple electron-optical columns.

In another embodiment, the set of electron-optical elements of the electron-optical column 106 includes one or more electron beam scanning elements 117. For example, the one or more electron beam scanning elements may include, but are not limited to, one or more electromagnetic scanning coils or electrostatic deflectors suitable for controlling a position of the beam 103 relative to the surface of the substrate 112. In this regard, the one or more scanning elements may be utilized to scan the electron beam 103 across the surface of the substrate 112.

In another embodiment, the system 100 includes a sample stage 114. The sample stage 114 secures the substrate 112. In another embodiment, the sample stage 114 is an actuatable stage. For example, the sample stage 114 may include, but is not limited to, one or more translational stages suitable for selectably translating the substrate 112 along one or more linear directions (e.g., x-direction, y-direction and/or z-direction) relative to the electron beam 103. By way of another example, the sample stage 114 may include, but is not limited to, one or more rotational stages suitable for selectably rotating the substrate 112 along a rotational direction. By way of another example, the sample stage 114 may include, but is not limited to, a rotational stage and a translational stage suitable for selectably translating the substrate 112 along a linear direction and/or rotating the substrate 112 along a rotational direction.

In this regard, the stage 114 may act to translate the substrate 112 relative to the electron beam 103. In turn, a cathodoluminescence signal is generated in the surface of the substrate 112. This cathodoluminescent signal may then be captured (discussed further herein) and correlated with the scan position of the electron beam 103 relative to the substrate 112, so that the cathodoluminescent signal provides information about the electron-probed spot/scan path. It is noted herein that the system 100 may operate in any scanning or spot detection mode known in the art. For example, the system 100 may operate in a "swathing" or "rastering" mode when scanning an electron beam 103 across the surface of the substrate 112. In this regard, the system 100 may scan an electron beam 103 across the surface of the substrate 112, while the sample is moving, with the direction of scanning being nominally perpendicular to the direction of the sample motion. By way of another example, the system 100 may operate in a step-and-scan mode when scanning an electron beam 103 across the surface of the substrate 112.

In another embodiment, the system 100 includes a set of guide optics 108 configured to collect the cathodoluminescent light 105 emitted by the substrate 112 in response to the electron beam 103. The guide optics 108 may further direct the cathodoluminescent light 105 to a set of collection optics 110. It is noted herein that the guide optics 108 may include any type of guide optics known in the art capable of capturing the cathodoluminescent light 105 emitted by the substrate 112 and, in turn, directing the cathodoluminescent light 105 to the collection optics 110. For example, the guide optics 108 may include, but are not limited to, a set of coaxial reflective optics (e.g., mirror-based optics arranged coaxially with respect to electron-optical axis) disposed within or below the electron-optical column 106. For instance, the guide optics 108 may include a reflective optical train positioned within or below the electron-optical column 106 and arranged to collect at least some of the cathodoluminescent light 105 emitted by the substrate 112 and direct the light 105 to the collection optics 110.

The collection optics 110 may include any collection optical elements known in the art suitable for receiving the cathodoluminescent light 105 from the guide optics 108 and imaging the light 105 onto the detector 116. For example, the collection optics 110 may include any number of lenses, mirrors, optical fiber bundles, optical guides and the like to direct light from the guide optics 108 to the detector 116. The detector 116 may include any detector known in the art suitable for detecting light. For example, the detector 116 may include, but is not limited to, a CCD detector, a TDI-CCD detector or a PMT detector.

In another embodiment, the system 100 includes a controller 118. The controller 118 may be communicatively coupled to the output of the one or more detectors 116. In one embodiment, the controller 118 includes one or more processors (not shown) configured to execute program instructions suitable for causing the one or more processors to execute one or more data processing steps described in the present disclosure. In one embodiment, the one or more processors of the controller 118 are in communication with a carrier medium (e.g., non-transitory storage medium (i.e., memory medium)) containing program instructions configured to cause the one or more processors of the controller 118 to carry out various steps described through the present disclosure. It should be recognized that the various processing steps described throughout the present disclosure may be carried out by a single computing system or, alternatively, a multiple computing system. The controller 118 may include, but is not limited to, a personal computer system, mainframe computer system, workstation, image computer, parallel processor, or any other device known in the art. In general, the terms "computing system" or "computer system" may be broadly defined to encompass any device having one or more processors, which execute instructions from a memory medium. Moreover, different subsystems of the system 100 may include a computer system or logic elements suitable for carrying out at least a portion of the steps described above. Therefore, the above description should not be interpreted as a limitation on the present disclosure but merely an illustration In one embodiment, the one or more processors of the controller 118 may receive the imagery data associated with the detected cathodoluminescent light 105 from the one or more detectors 116. In turn, the one or more processors of the controller 118 may execute a set of program instructions to analyze one or more characteristics of the detected cathodoluminescent light 105. In one embodiment, the controller 118 may carry out defect detection based on the received imagery data. For example, the one or more processors may identify and/or analyze the defect sites observed with the cathodoluminescent light 105. For instance, the one or more processors may count the number of defects in a selected area of the substrate through the analysis of the cathodoluminescence-based imagery data. In another instance, the one or more processors may calculate the defect density in a selected area of the substrate through the analysis of the cathodoluminescence-based imagery data.

In another embodiment, the detector 116 and/or controller 118 may form a panchromatic of the substrate 112 with the cathodoluminescent light 105. In this regard, the detector 116 may capture image data across multiple wavelengths of cathodoluminescent light 105. In a panchromatic image, defective sites appear as dark spots and counting the dark spots may reveal the density of defects which will impact device performance. In another embodiment, the detector 116 and/or controller 118 may form a monochromatic image of the substrate 112 with the cathodoluminescent light 105. In this regard, the detector 116 may capture image data for a single wavelength range of the cathodoluminescent light 105.

In another embodiment, the detector 116 and/or controller 118 may perform hyperspectral imaging of the substrate 112 based on the measured cathodoluminescence light 105. For example, the detector 116 and/or controller 118 may form images having spectral resolution of approximately 10 nm. Further, the controller 118 may then spectrally decompose the image data from the detector 118 so as to analyze the inspection data (e.g., presence, number, density of defects) for images of different wavelengths.

In another embodiment, the controller 118 may perform a temporal decay analysis on the measured cathodoluminescence light 105. For example, the controller 118 may measure the temporal decay of the light curve associated with the cathodoluminescence light 105. For instance, the decay of the cathodoluminescent light curve may be measured as a function of the time after the electron beam 103 initiated cathodoluminescent light emission from the substrate 112.

In another embodiment, the system 100 may perform depth-resolved spectroscopy on the substrate 112. For example, the energy of the electron beam 103 may be adjusted in order to vary the depth the electron beam 103 penetrates the substrate 112. In this regard, the controller 118 utilizing the known energy of the beam 103 (and thus the depth of penetration) may correlate the cathodoluminescent signal received from the detector 116 to the associated energy/penetration depth of the electron beam 103.

It is further noted herein that an optical assembly including the guide optics 108, the collection optics 110, the detector 116 and/or controller 118 may be coupled to a pre-existing electron beam inspection or review tool. In this regard, pre-existing electron beam inspection or review tools may be augmented with the ability to detect cathodoluminescence provided by the guide optics 108, the collection optics 110, detector 116 and/or the controller 118.

Figure 2:
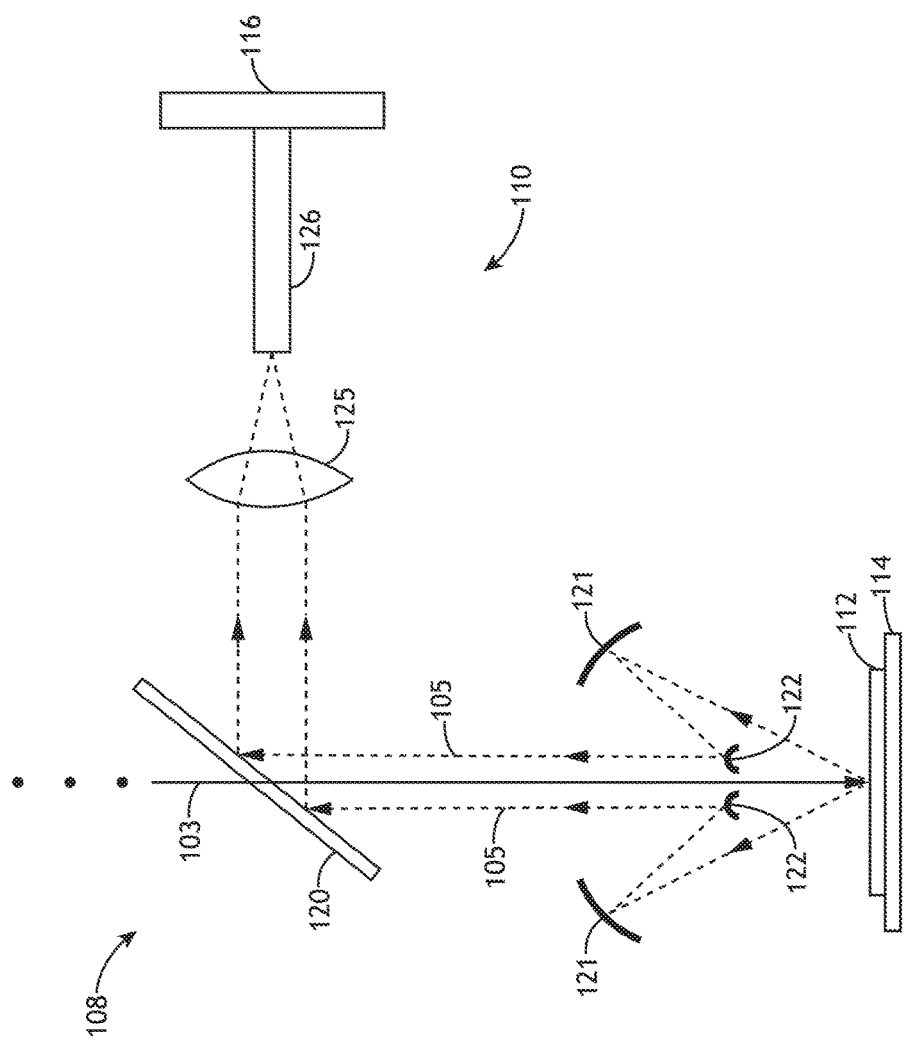
FIG. 2 is a simplified schematic view illustrating the cathodoluminescent light path through the guide optics and the collection optics to the detector, in accordance with one embodiment of the present disclosure.

FIG. 2 illustrates a set of guide optics 108 and a set of collection optics 110 suitable for implementation in system 100, in accordance with one or more embodiments of the present disclosure. The guide optics 108 and collection optics 110 are parts of the inspection sub-system 102 and the overall system 100 for measuring cathodoluminescence for substrate defect inspection.

In one embodiment, the guide optics 108 include an apertured plane mirror 120, incurved mirror 121 and/or a biconvex mirror 122. In one embodiment, the incurved mirror 121 captures at least some of the cathodoluminescent light 105 emitted from the substrate 112 in response to the electron beam 103 impinging on the substrate 112. In another embodiment, the incurved mirror 121 directs at least some of the captured cathodoluminescent light toward the biconvex mirror 122. In another embodiment, the biconvex mirror 122 directs at least some of the cathodoluminescent light toward the aperture plane mirror 120. In another embodiment, at least some of the cathodoluminescent light 105 incident on the aperture plane mirror 120 is directed toward the focusing lens 125. In one embodiment, the focusing lens 125 of the collection optics 110 acts to image the cathodoluminescent light 105 onto the optical fiber 126 coupled to the detector 116.

The description of the guide optics 108 and collection optics 110 provided above should not be interpreted as a limitation on the scope of the present disclosure and is provided merely for purposes of illustration. The set of guide optics 108 and collection optics 110 may include any component known in the art suitable for collecting, focusing and/or directing the cathodoluminescent light 105 to the detector 116. Further, the scope of the present disclosure is not limited to the use of reflective-type guide optics. It is recognized herein that the guide optics 108 of system 100 may be extended to include transmissive optical elements and/or a combination of transmissive and reflective optical elements. For instance, any combination of one or more lenses, internal reflecting prisms and/or light guides may be used to guide cathodoluminescent light from the substrate 112 to the collections optics 110 and toward the detector 116.

Figure 3:
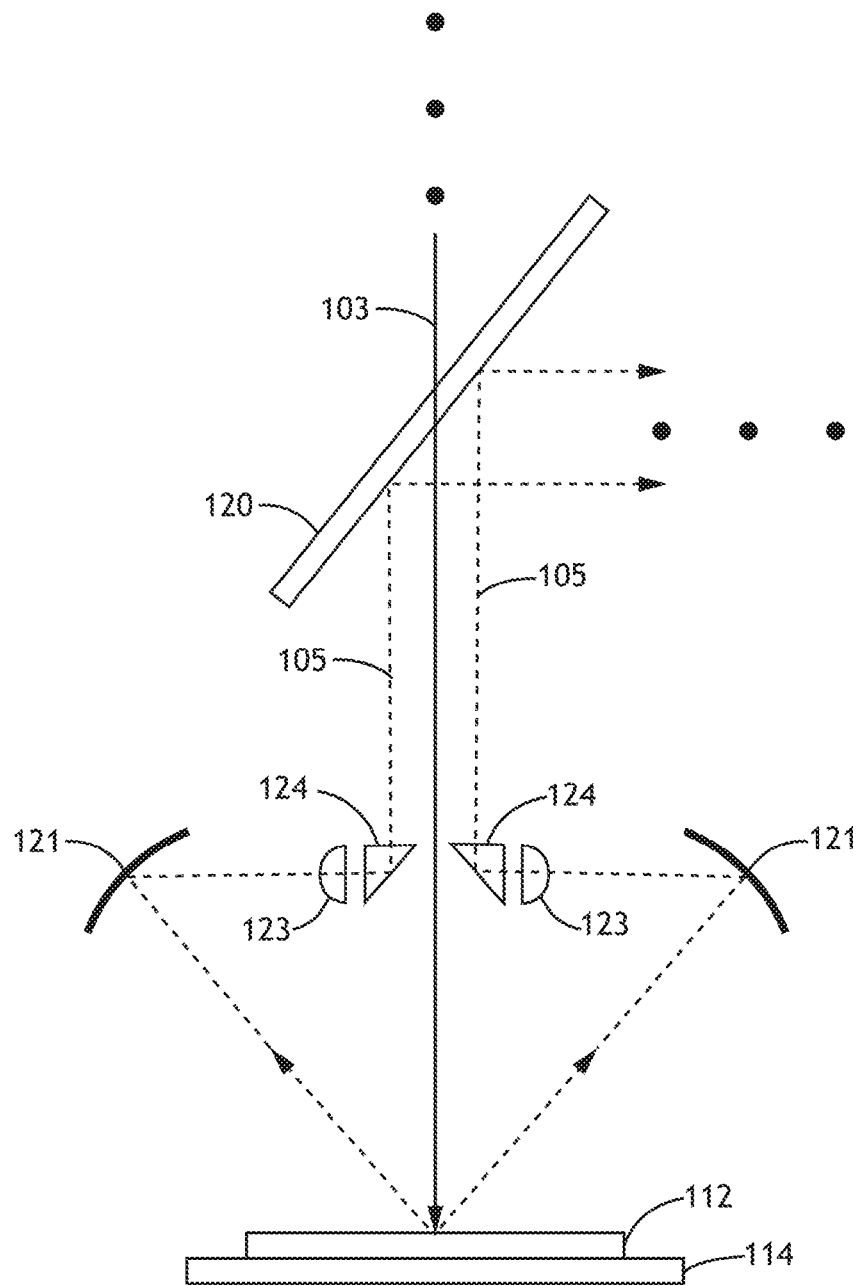
FIG. 3 is a simplified schematic view illustrating the cathodoluminescent light path through the guide optics, in accordance with one embodiment of the present disclosure.

FIG. 3 illustrates a set of guide optics 108 including one or more transmissive components, in accordance with one or more embodiments of the present disclosure. In one embodiment, the guide optics 108 includes a plano convex lens 123 and a right-angle prism 124 arranged to guide cathodoluminescent light from the substrate 112 to the aperture plane mirror 120. The optical arrangement depicted in FIG. 3 should not be interpreted as a limitation on the scope of the present disclosure and is provided merely for illustrative purposes.

Figure 4:
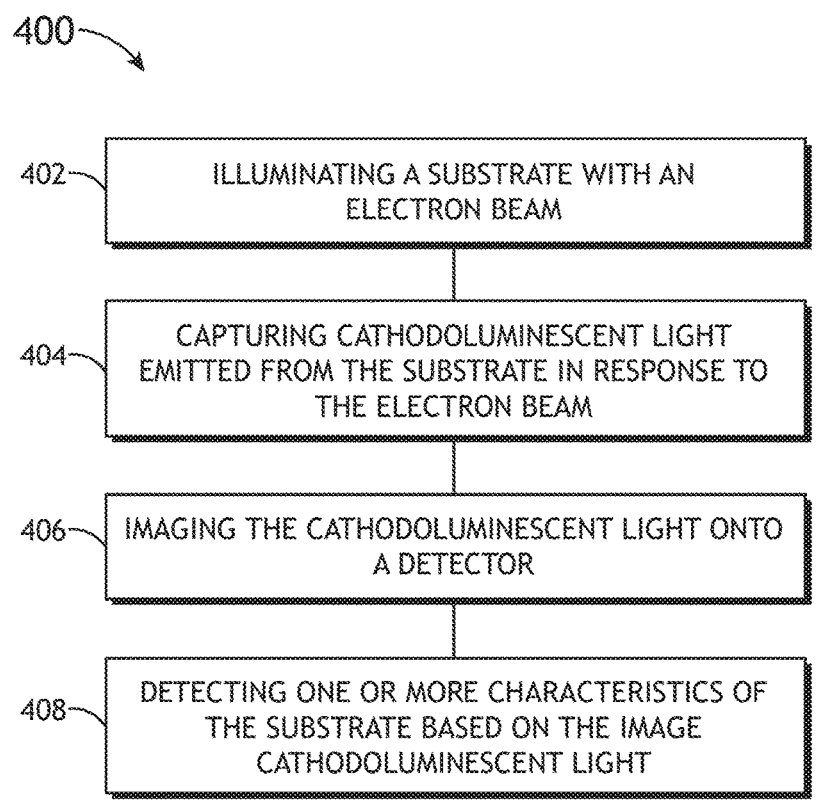
FIG. 4 is a flow diagram illustrating a method for measuring cathodoluminescence from a substrate, in accordance with one embodiment of the present disclosure.

FIG. 4 illustrates a flow diagram depicting a method for measuring cathodoluminescence from a substrate, in accordance with one or more embodiments of the present disclosure. It is recognized that steps of the process flow 400 may be carried out via system 100. It should, however, be recognized that the system 100 should not be interpreted as a limitation on process 400 as it is contemplated that a variety of system configurations may carry out process flow 400. Step 402 includes illuminating a substrate with an electron beam. For example, as show in FIG. 1, electron source 104 may generate one or more electron beams 103, which is then directed onto the substrate 112 via the electron-optical column 106. Step 404 includes capturing cathodoluminescent light emitted from the substrate in response to the electron beam. For example, as show in FIG. 1, cathodoluminescent light 105 emitted from the substrate 112 may be directed from the substrate by the guide optics 108 to the collection optics 110. For instance, as shown in FIG. 2, the incurved mirror 121, biconvex mirror 122 and aperture plane mirror 120 direct cathodoluminescent light from the substrate 112 to the focusing lens 125. Step 406 includes imaging the cathodoluminescent light onto a detector. For example, as shown in FIG. 1, the collection optics 110 direct cathodoluminescent light to the detector 116. For instance, as shown in FIG. 2, the focusing lens 125 directs cathodoluminescent light 105 onto the optical fiber 126 that is coupled to the detector 113. Step 408 includes detecting one or more characteristics of the substrate 112 based on the imaged cathodoluminescent light 105. For example, as shown in FIG. 1, the detector 116 may sent one or more data signals indicative of the cathodoluminescent light 105 to the controller 118 that may execute a set of program instructions to locate defects on the substrate 112. For instance, as shown in FIG. 1, the detector 116 may send one or more data signals indicative of the cathodoluminescent light 105 to the controller 118 that may execute a set of program instructions to perform hyper-spectral imaging, analyze signal lifetime or determine defect density on the substrate 112.

All of the methods described herein may include storing results of one or more steps of the method embodiments in the memory. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the disclosure is defined by the appended claims

What is claimed is:

1. An apparatus comprising:
   an electron beam source configured to generate an electron beam;
   a sample stage configured to secure a sample;
   an electron-optical column including a set of electron-optical elements to direct at least a portion of the electron beam onto a portion of the sample;
   a set of guide optics located at a position within or below the electron-optical column, wherein the set of guide optics comprises a first coaxial mirror and a second coaxial mirror, wherein the first coaxial mirror is configured to receive cathodoluminescent light from the sample and direct the cathodoluminescent light to the second coaxial mirror;
   a set of collection optics, wherein the set of guide optics is configured to direct the cathodoluminescent light collected from the sample to the set of collection optics; and
   a detector, wherein the set of collection optics is configured to image the cathodoluminescent light onto the detector.

2. The apparatus of claim 1, wherein the electron beam source comprises:
   one or more electron guns.

3. The apparatus of claim 1, wherein the set of electron-optical elements of the electron-optical column comprises:
   at least one of a condenser lens, a scanning element or an objective lens.

4. The apparatus of claim 1, wherein the detector comprises:
   at least one of a spectrometer, a CCD, a TDI-CCD or a PMT.

5. The apparatus of claim 1, wherein the detector comprises
   a single detector.

6. The apparatus of claim 1, wherein the detector comprises:
   an array of detectors.

7. The apparatus of claim 1, further comprising:
   a controller communicatively coupled to the detector.

8. The apparatus of claim 7, wherein the controller comprises:
   one or more processors configured to execute program instructions to determine one or more characteristics of the substrate based on the imaged cathodoluminescent light.

9. The apparatus of claim 1, wherein the first mirror comprises:
   an incurve mirror.

10. The apparatus of claim 1, wherein the second mirror comprises:
    biconvex mirror.

11. The apparatus of claim 1, wherein the set of guide optics comprises:
    a coaxial apertured plane mirror.

12. The apparatus of claim 1, wherein the set of collection optics comprise:
    at least one of reflective optics or transmissive optics.

13. The apparatus of claim 1, wherein the set of collection optics comprise:
    at least one of a lens, mirror, optical fiber bundle or optical guide.

14. The apparatus of claim 1, wherein the sample comprises:
    a sample displaying cathodoluminescence in response to an electron beam.

15. The apparatus of claim 1, wherein the sample comprises:
    an epitaxial film formed on a semiconductor wafer.

16. The apparatus of claim 15, wherein the sample comprises:
    at least one of a patterned semiconductor wafer or unpatterned semiconductor wafer.

17. The apparatus of claim 1, wherein the sample stage comprises:
    one or more actuatable stages translatable in at least one of the x-direction, y-direction or z-direction.

18. The apparatus of claim 1, wherein the sample stage comprises:
    one or more rotatable stages.

19. A method of cathodoluminescent-based inspection comprising:
    illuminating a substrate with an electron beam;
    capturing, with a set of guide optics, cathodoluminescent light emitted from the substrate in response to the electron beam, wherein the set of guide optics comprises a first coaxial mirror and a second coaxial mirror, wherein the first coaxial mirror is receives cathodoluminescent light from the sample and directs the cathodoluminescent light to the second coaxial mirror;
    imaging the cathodoluminescent light onto a detector; and
    determining one or more characteristics of the substrate based on the imaged cathodoluminescent light.

20. The method of claim 19, wherein the determining one or more characteristics of the substrate based on the imaged cathodoluminescent light comprises:
    detecting one or more defects of the substrate based on the imaged cathodoluminescent light.

21. The method of claim 19, wherein the determining one or more characteristics of the substrate based on the imaged cathodoluminescent light comprises:

determining at least one the defect density or number of defects in an image formed from the cathodoluminescent light.

22. The method of claim 19, wherein the determining one or more characteristics of the substrate based on the imaged cathodoluminescent light comprises:

performing depth-resolved cathodoluminescent light spectroscopy on the cathodoluminescent light.

23. The method of claim 19, wherein the determining one or more characteristics of the substrate based on the imaged cathodoluminescent light comprises:

performing spectral decomposition of the cathodoluminescent light.

24. The method of claim 19, wherein the determining one or more characteristics of the substrate based on the imaged cathodoluminescent light comprises:

performing temporal decay analysis of the cathodoluminescent light.

* * * * *